(12) United States Patent
Jayaraman et al.

(10) Patent No.: US 9,969,721 B2
(45) Date of Patent: May 15, 2018

(54) PROCESS FOR THE PREPARATION OF VILAZODONE HYDROCHLORIDE AND ITS AMORPHOUS FORM

(71) Applicant: ALEMBIC PHARMACEUTICALS LIMITED, Vadodara-Gujarat (IN)

(72) Inventors: Venkat Raman Jayaraman, Vadodara-Gujarat (IN); Dhiraj Rathod, Vadodara-Gujarat (IN); Irfan Vohra, Vadodara-Gujarat (IN); Vinayak Bhujade, Vadodara-Gujarat (IN); Viral Modi, Vadodara-Gujarat (IN); Mayur Budh, Vadodara-Gujarat (IN); Ojas Gandhi, Vadodara-Gujarat (IN)

(73) Assignee: Alembic Pharmaceuticals Limited, Vadodara-Gujarat (IN)

( * ) Notice: Subject to any disclaimer, the term of this patent is extended or adjusted under 35 U.S.C. 154(b) by 301 days.

(21) Appl. No.: 14/394,084

(22) PCT Filed: Apr. 5, 2013

(86) PCT No.: PCT/IB2013/052729
§ 371 (c)(1),
(2) Date: Oct. 11, 2014

(87) PCT Pub. No.: WO2013/153492
PCT Pub. Date: Oct. 17, 2013

(65) Prior Publication Data
US 2015/0087835 A1    Mar. 26, 2015

(30) Foreign Application Priority Data

Apr. 12, 2012 (IN) .......................... 1187/MUM/2012
Jun. 21, 2012 (IN) .......................... 1784/MUM/2012

(51) Int. Cl.
*C07D 403/12*    (2006.01)
*C07D 403/14*    (2006.01)
*C07D 405/12*    (2006.01)

(52) U.S. Cl.
CPC ......... *C07D 405/12* (2013.01); *C07D 403/12* (2013.01); *C07D 403/14* (2013.01)

(58) Field of Classification Search
CPC ... C07D 403/12; C07D 403/14; C07D 405/12
See application file for complete search history.

(56) References Cited

U.S. PATENT DOCUMENTS

| | | | | |
|---|---|---|---|---|
| 5,532,241 | A | * 7/1996 | Bottcher | ............. C07D 405/14 514/254.09 |
| 2013/0324554 | A1 | 12/2013 | Mohan Rao et al. | |
| 2014/0323498 | A1 | * 10/2014 | Leksic et al. | ............ 514/254.09 |

FOREIGN PATENT DOCUMENTS

| | | |
|---|---|---|
| CN | 102219783 A | 10/2011 |
| CN | 102267985 A | 12/2011 |
| EP | 0648767 A1 | 4/1995 |
| WO | WO-2002/102794 A2 | 12/2002 |
| WO | WO-2012131706 A1 | 10/2012 |
| WO | WO-2013078361 A1 | 5/2013 |
| WO | WO-2013088373 A1 | 6/2013 |
| WO | WO-2013168126 A1 | 11/2013 |

OTHER PUBLICATIONS

Bin, Hu, et al., "Scale-Up Synthesis of Antidepressant Drug Vilazodone", Organic Process Research & Development, vol. 16, No. 9, Sep. 21, 2012.
Heinrich, T. et al., "Synthesis and Structure-Activity Relationship in Class of Indolebutylpiperazines as Dual 5-HT1A Receptor Agonists and Serotonin Reuptake Inhibitors", Journal of Medicinal Chemistry, American Chemical Society, US, vol. 47, No. 19, pp. 4684-4692, Jan. 1, 2004.
Sorbera, L. et al., "Vilazodone Hydrochloride", Drugs of the Future, Prous Science, ES, Jan. 1, 2001, vol. 26, No. 3, pp. 247-252.
International Search Report dated Nov. 20, 2013 for International Application No. PCT/IB2013/052729.

* cited by examiner

*Primary Examiner* — Sun Jae Yoo
(74) *Attorney, Agent, or Firm* — Schiff Hardin LLP

(57) ABSTRACT

The present invention relates to an improved process for the preparation of vilazodone Hydrochloride and a process for preparation of novel pure amorphous form of vilazodone hydrochloride.

8 Claims, 3 Drawing Sheets

PROCESS FOR THE PREPARATION OF VILAZODONE HYDROCHLORIDE AND ITS AMORPHOUS FORM

RELATED APPLICATION

This application claims the benefit of priority of our Indian patent application numbers 1187/MUM/2012 filed on 12 Apr. 2012 and 1784/MUM/2012 filed on 21 Jun. 2012 which are incorporated herein by reference.

FIELD OF THE INVENTION

The present invention relates to an improved, commercially viable and industrially advantageous process for the preparation of Vilazodone or a pharmaceutically acceptable salt thereof in high yield and purity. More specifically the present invention relates to an improved and industrially advantageous process for the preparation of Vilazodone Hydrochloride. The present invention also provides a novel pure amorphous form of vilazodone hydrochloride, process for preparation, pharmaceutical compositions, and method of treating thereof.

BACKGROUND OF THE INVENTION

Vilazodone is 5-(4-[4-(5-cyano-1H-indol-3-yl)butyl]piperazin-1-yl)benzofuran-2-carboxamide and represented by formula (I).

The product is marketed in the form of Hydrochloride salt. The current pharmaceutical product containing this drug is being sold by Merck using the trade name Viibryd. Vilazodone is an SSRI antidepressant developed by Clinical Data for the treatment of major depressive disorder.

Vilazodone was first described in U.S. Pat. No. 5,532,241. Example 4 of Said patent described process for preparing vilazodone by reacting 1-[4-{5-cyanoindol-3-yl)butyl]-4-{2-carboxybenzofuran-5-yl)-piperazine at first with 2-chloro-1-methylpyridinium methanesulfonate in N-methylpyrrolidine and then with dried ammonia. Customary working up gives the free base vilazodone. Which is further converted in to Vilazodone hydrochloride.

Journal of Medicinal Chemistry (2004), 47(19), 4684-4692 disclose process for preparation of vilazodone as per below scheme.

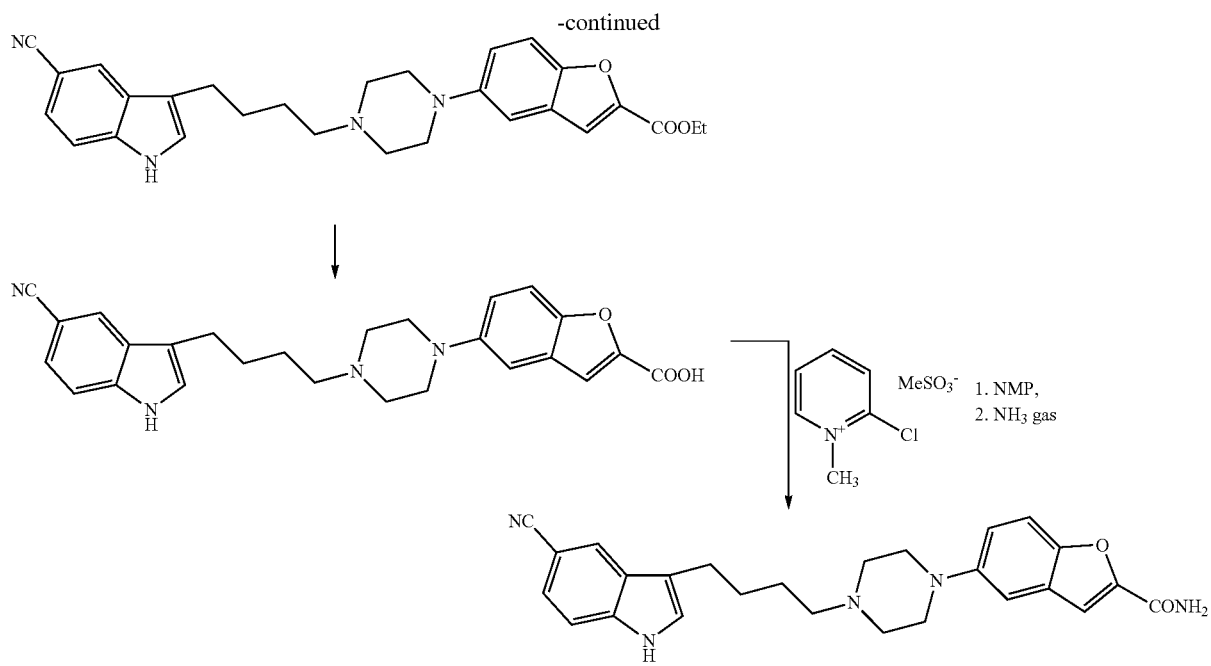
Org. Process Res. Dev., 2012, 16 (9), pp 1552-1557 discloses process as per below scheme.
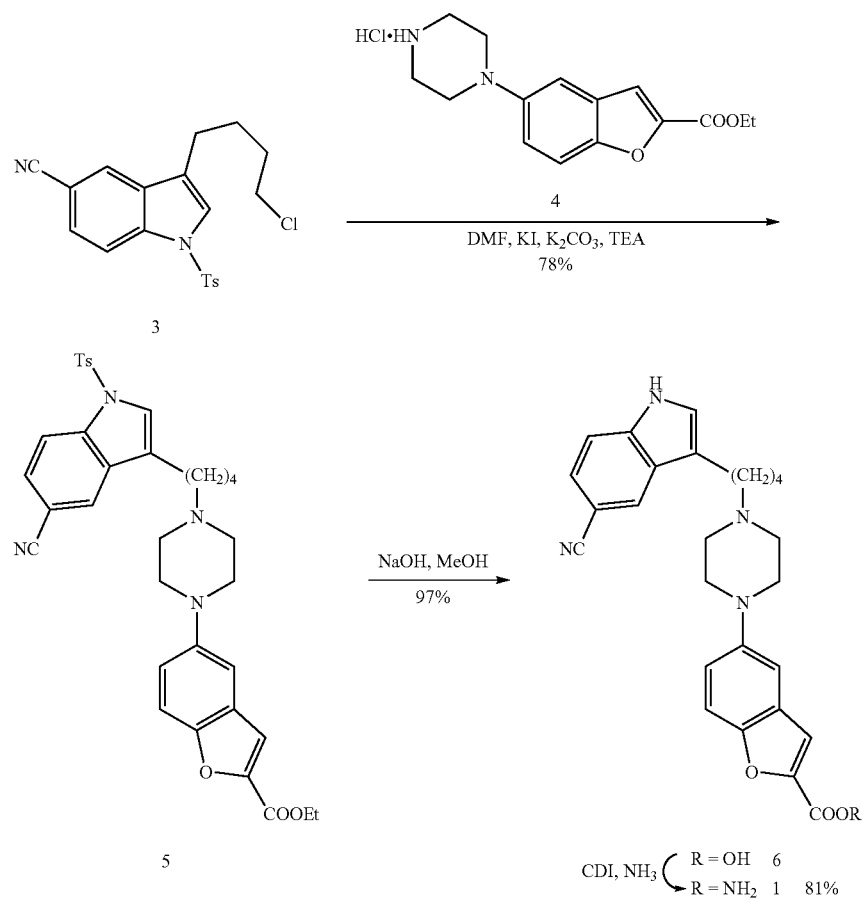

The main problem associated with these processes is that it involves use of less economical reagent such as 2-chloro-1-methylpyridinium methane sulphonate and solvent such as N-methyl pyrrolidine.

Zhongguo Yaowu Huaxue Zazhi (2012), 22(1), 74-75, 81 discloses many possible ways for synthesis of vilazodone.

None of the prior art disclosing direct conversion of ester to amide. All prior art references shows first conversion of ester of compound of formula II in to corresponding acid and then reaction of acid with ammonia in presence of solvent and catalyst to prepare vilazodone.

Org. Process Res. Dev., 2012, 16 (9), pp 1552-1557 article disclose that no vilazodone was obtained during direct conversion of ester to amide.

The above processes for preparation of Vilazodone require many numbers of steps and involve unfriendly reagents. The process is less economical, relatively less safe and time-consuming. Hence such technology is not readily suitable for commercial production. Therefore, the present invention provides a process in which directly ester converts in to amide.

PCT publication no. WO2002102794A2 describes different polymorphs of Vilazodone hydrochloride, termed as form I to form XVI. WO2002102794A2 describes form XVI as amorphous form. The term "amorphous" means a solid without long-range crystalline order. However, the X-ray powder diffraction pattern of form XVI shows that the polymorph is not in its pure amorphous form but also comprises crystalline peaks. Therefore, it does not demonstrate the amorphous nature of the product. It is essentially a mixture of crystalline and amorphous form which is not a form of suitable choice.

Polymorphic purity is one of the important aspects in the development of any active pharmaceutical ingredients. An active pharmaceutical ingredient is always preferred to have consistency in terms of polymorphic purity. Therefore it is desirable to have either pure crystalline form or a substantially pure amorphous form.

Solvent medium and mode of isolation play very important role in obtaining a polymorphic form over the other.

Accordingly, there remains a need in the art for a novel, stable and substantially pure amorphous form of Vilazodone hydrochloride. The present inventors have directed its research work to get the desired polymorphic purity.

Based on the aforementioned drawbacks, prior art processes found to be unsuitable for preparation of vilazodone at lab scale and commercial scale operations. Hence, a need still remains for an improved and commercially viable process of preparing pure vilazodone or a pharmaceutically acceptable salt thereof that will solve the aforesaid problems associated with process described in the prior art and will be suitable for large-scale preparation, in lesser reaction time, in terms of simplicity, purity and yield of the product.

SUMMARY OF THE INVENTION

The present inventors have focused on the problems associated with the prior art processes and have developed an improved process for the preparation of vilazodone.

As a whole, a process such as the one provided by the present invention has the advantage of high yields is achieved with very simple steps. Likewise, said process is not toxic and allows starting from inexpensive and non-hazardous reactants, providing vilazodone, with a good yield and pharmaceutical quality. All of this contributes in reducing the overall cost of the process, making it commercially interesting and allowing it to be put into practice on an industrial level.

Therefore, in one aspect the present invention provides a process for preparing vilazodone or a salt thereof, comprising a step of obtaining a compound of formula I or a salt there of, from compound of formula II.

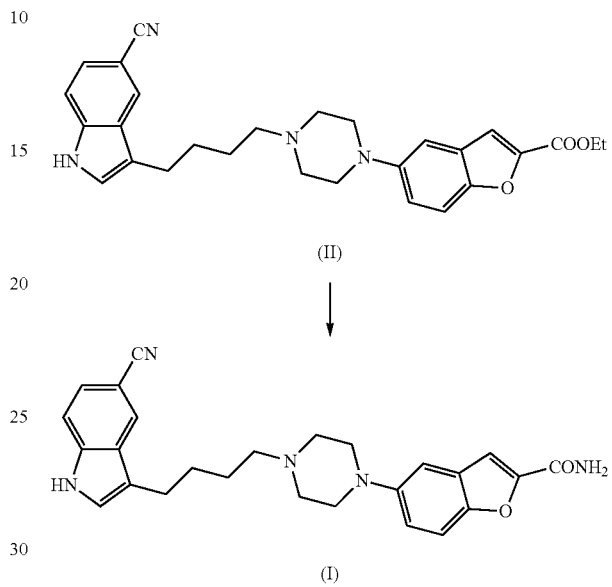

Therefore, in another aspect the present invention provides a process for preparation of vilazodone a compound of formula (I) or a salt thereof, comprising a step of reacting compound of formula II with source of ammonia to get a compound of formula (I).

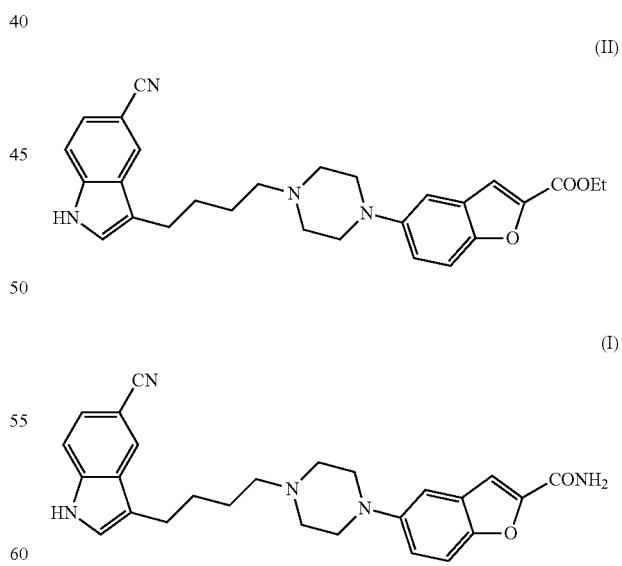

Therefore, in another aspect the present invention provides a process for preparation of vilazodone or a salt thereof, comprising a step of obtaining a compound of formula I or a salt there of, from compound of formula II in presence of source of ammonia and any suitable solvent.

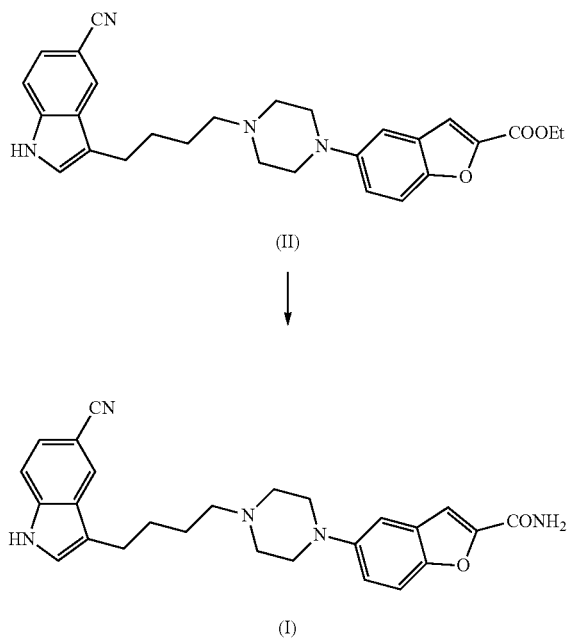 [SMILES: CCOC(=O)c1cc2cc(N3CCN(CCCCc4c[nH]c5ccc(C#N)cc45)CC3)ccc2o1 ; "(II)" ; N#Cc1ccc2[nH]cc(CCCCN3CCN(c4ccc5oc(C(N)=O)cc5c4)CC3)c2c1 ; "(I)"]

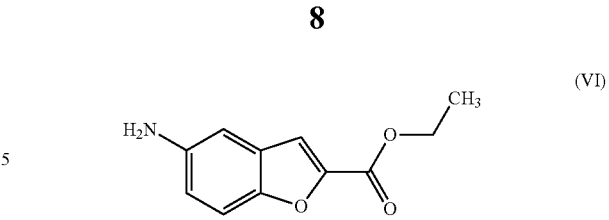

Source of ammonia is selected from ammonia gas, liquid ammonia, aqueous ammonia, ammonium hydroxide, magnesium nitride and formamide with base; more preferably ammonia gas. Suitable solvent is selected from water, alcohols, ketones, diols, triols, esters, amides, ethers, hydrocarbons, polar aprotic solvents, polar solvents, chloro solvents, nitriles or mixtures thereof. polar aprotic solvents such as acetone, DMF, acetonitrile, DMSO, sulfolane; alcohols such as methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether, N,N,-dimethyl acetamide, PEG 300, propylene glycol; chloro solvents like methylene chloride, chloroform and ethylene chloride; hydrocarbon solvents like toluene, xylene, heptane, cyclohexane and hexane; more preferably DMSO.

Therefore, in another aspect the present invention provides a process for preparation of vilazodone or a salt thereof, comprising a step of obtaining a compound of formula I or a salt there of, from compound of formula II in presence suitable solvent under ammonia gas pressure.

Therefore, in another aspect the present invention provides a novel compound ethyl 5-(1-piperazinyl)-benzofuran-2-carboxylate dihydrochloride.

Therefore, in another aspect the present invention provides a novel compound ethyl 5-(1-piperazinyl)-benzofuran-2-carboxylate hydrobromide.

Therefore, in another aspect the present invention provides a process for preparation of ethyl 5-(1-piperazinyl)-benzofuran-2-carboxylate dihydrochloride comprises reaction of compound of formula (VI) with Bis(2-chloroethyl) amine hydrochloride in presence of suitable base, suitable solvent and phase transfer catalyst.

Phase transfer catalyst is selected from the group consisting of quaternary ammonium cations, quaternary phosphonium cations, and cyclic polyethers such as tricaprylylmethylammonium chloride, methyl tributyl ammonium chloride, methyl tributyl ammonium fluoride, tetrabutyl ammonium bromide, tetrabutyl ammonium fluoride, tetrabutyl ammonium hydrogen sulfate, triethyl benzyl ammonium chloride, tetrabutyl phosphonium bromide, tetrabutyl phosphonium chloride, tetraoctylphosphonium bromide, and mixtures thereof. Suitable solvent is selected from water, alcohols, ketones, diols, triols, esters, amides, ethers, hydrocarbons, polar aprotic solvents, polar solvents, chloro solvents, nitriles or mixtures thereof. Polar aprotic solvents such as acetone, DMF, acetonitrile, DMSO, sulfolane; alcohols such as methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether, N,N,-dimethyl acetamide, PEG 300, propylene glycol; chloro solvents like methylene chloride, chloroform and ethylene chloride; hydrocarbon solvents like toluene, xylene, heptane, cyclohexane and hexane, more preferably DMSO. Suitable base is selected from the group of alkali or alkaline earth metal hydroxide, carbonate, bicarbonate.

Therefore, in another aspect the present invention provides a process for preparation of vilazodone or a salt thereof, comprising purification of vilazodone base with any suitable solvent and suitable base optionally in presence of water, wherein suitable solvent is selected from group of polar aprotic solvents such as acetone, DMF, acetonitrile, DMSO, sulfolane, DMAC, NMP etc. Suitable base is selected from the group of alkali or alkaline earth metal hydroxide, carbonate, bicarbonate. wherein the suitable base is selected from NaOH, KOH, LiOH, NaHCO$_3$, KHCO$_3$, LiHCO$_3$, Na$_2$CO$_3$, K$_2$CO$_3$, Li$_2$CO$_3$, Mg(OH)$_2$, Ca(OH)$_2$, CaCO$_3$, MgCO$_3$, Ba(OH)$_2$, Be(OH)$_2$, BaCO$_3$, SrCO$_3$ and the like or mixtures thereof.

Therefore, in another aspect the present invention provides a process for preparation of vilazodone or a salt thereof, comprising purification of vilazodone base by treatment of vilazodone base with DMF and aqueous sodium hydroxide solution.

Therefore, in another aspect the present invention provides a novel compound process for preparation of vilazodone or a salt thereof, comprising crystallizing vilazodone base from DMSO and water.

Therefore, in another aspect the present invention provides a process having a content of 5-(4-[4-(5-cyano-1H-indol-3-yl)butyl]piperazin-1-yl)benzofuran-2-carboxylic acid is less than 1% by mole; more preferably less than 0.5% by mole; more specifically less than 0.15% by mole.

Therefore, in another aspect the present invention provides a novel compound novel crystalline form A of Vilazodone.

Therefore, in another aspect the present invention provides a novel compound Crystalline form A of Vilazodone, having an X-ray diffraction pattern comprising at least five peaks selected from 2theta values 5.8, 13.9, 18.6, 20.9, 21.9±0.3.

Therefore, in another aspect the present invention provides a process for preparing crystalline form A of vilazodone base, comprising the steps of: (a) dissolving vilazodone base in one or more organic solvent(s), (b) causing crystalline form A to precipitate from the solution obtained in step (a), and (c) isolating the crystalline form A obtained in step (b).

Therefore, in another aspect the present invention provides a novel compound amorphous vilazodone base.

Therefore, in another aspect the present invention provides a process for preparing amorphous vilazodone base, comprising the steps of: (a) dissolving vilazodone base in one or more organic solvent(s), (b) causing an amorphous solid to precipitate from the solution obtained in step (a), and (c) isolating the amorphous solid obtained in step (b).

Therefore, in another aspect the present invention provides a novel crystalline form II of ethyl 5-(4-(4-(5-cyano-1H-indol-3-yl)butyl)piperazin-1-yl)benzofuran-2-carboxylate hydrochloride.

Therefore, in another aspect the present invention provides a novel compound Crystalline form II of ethyl 5-(4-(4-(5-cyano-1H-indol-3-yl)butyl)piperazin-1-yl)benzofuran-2-carboxylate hydrochloride, having an X-ray diffraction pattern comprising at least five peaks selected from 2theta values 11.7, 18.86, 22.75, 23.3, 24.7±0.3.

Therefore, in another aspect the present invention provides a process for preparation of vilazodone comprises condensation of compound of formula (VII) or salt thereof with compound of formula (VIII) to get compound of formula (II) or salt thereof in presence of triethyl amine and tetrabutyl ammonium bromide.

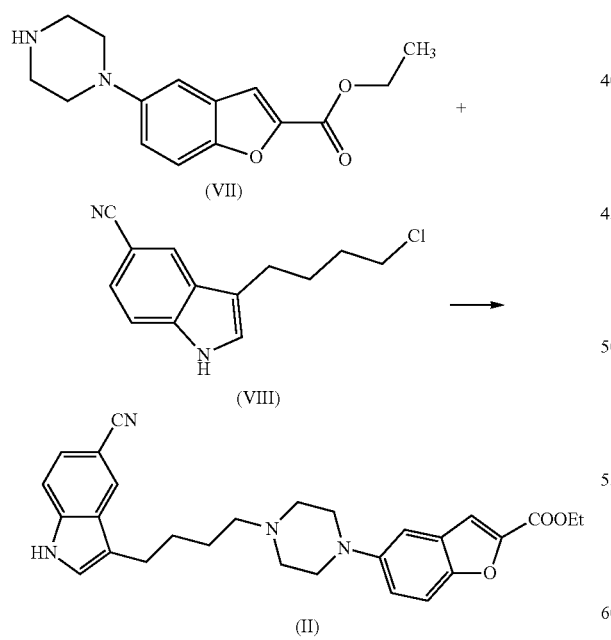

Therefore, in another aspect the present invention provides a process for preparation of vilazodone comprises condensation of compound of formula (VII) hydro bromide salt with compound of formula (VIII) to get compound of formula (II).

Therefore, in another aspect the present invention provides a process for the preparation of vilazodone or a salt thereof which comprises, a. reacting 5-nitro salicaldehyde of formula (III) with 2-bromo diethyl malonate of formula (IV) to get compound of formula (V),

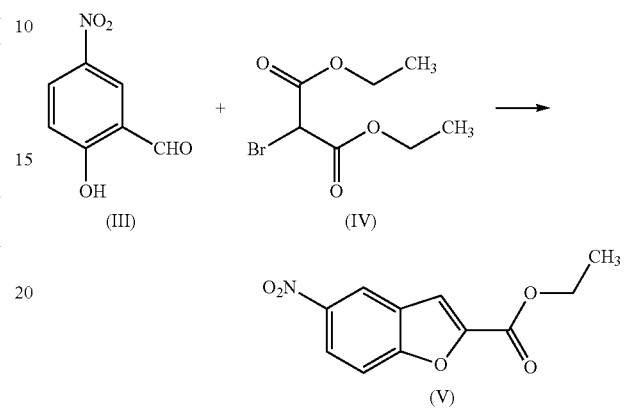

b. reducing compound of formula (V) to get compound of formula (VI)

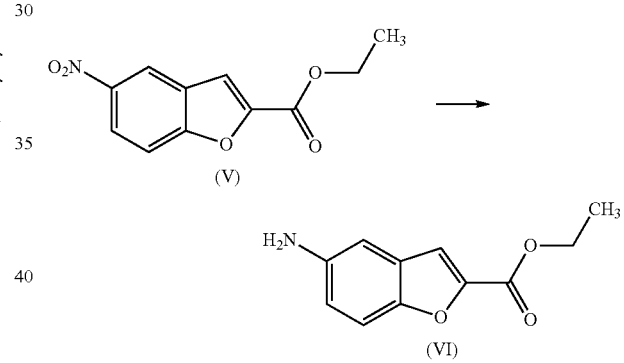

c. converting compound of formula (VI) to compound of formula (VII),

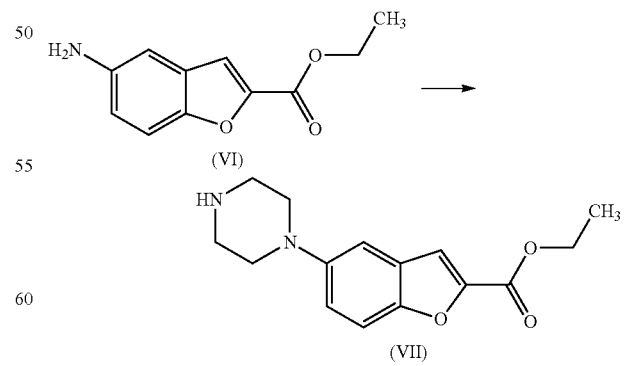

d. Condensing compound of formula (VII) or salt thereof with compound of formula (VIII) to get compound of formula (II) or salt thereof,

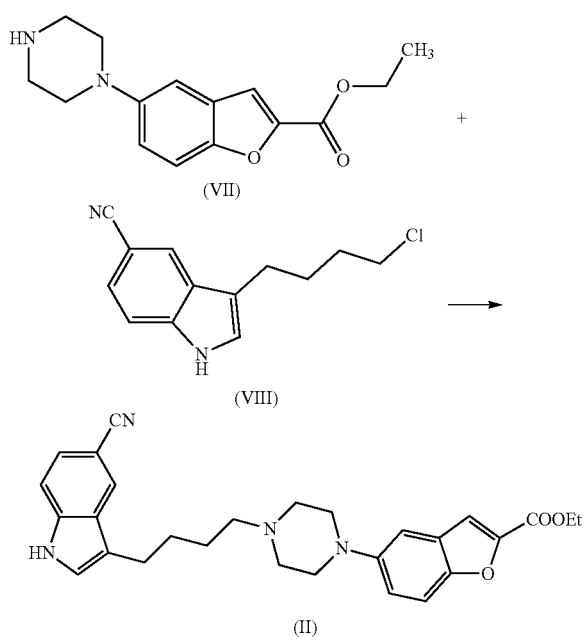

e. reacting compound of formula (II) with source of ammonia to get compound of formula (I)

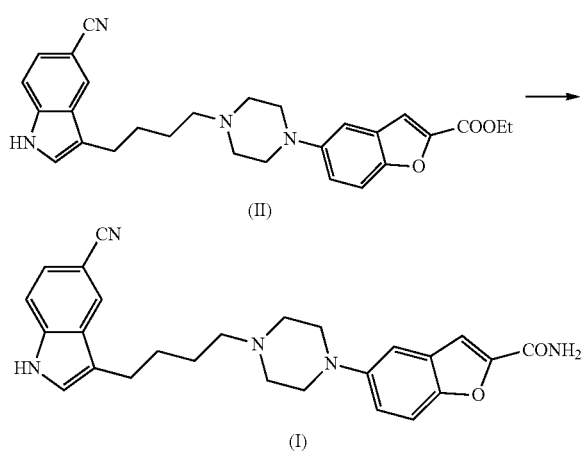

The present inventors have now surprisingly and unexpectedly discovered a novel pure amorphous form of Vilazodone hydrochloride with high purity, adequate stability and good dissolution properties.

In one aspect, the present invention provides a novel, pure and stable amorphous form of Vilazodone hydrochloride.

In one aspect, the present invention provides a novel, pure and stable amorphous form of Vilazodone hydrochloride characterized by X-ray diffraction pattern as depicted in FIG. 1.

In another aspect, the present invention provides a pharmaceutical composition comprising amorphous Vilazodone hydrochloride of the present invention and one or more pharmaceutically acceptable excipients.

In another aspect, the amorphous Vilazodone hydrochloride disclosed herein for use in the pharmaceutical compositions of the present invention, wherein 90 volume-percent of the particles (D90) have a size of less than or equal to about 500 microns, specifically less than or equal to about 300 microns, more specifically less than or equal to about 200 microns, still more specifically less than or equal to about 100 microns, and most specifically less than or equal to about 15 microns.

In another aspect, the present invention further encompasses a process for preparing the highly pure and stable amorphous form of Vilazodone hydrochloride.

In another aspect present invention provides a process for preparation of a stable and substantially pure amorphous form of Vilazodone hydrochloride, which comprises:
a) Providing a solution of Vilazodone hydrochloride in a suitable solvent or a mixture of solvents capable of dissolving Vilazodone hydrochloride;
b) Optionally, filtering the solvent solution to remove any extraneous matter; and
c) Substantially removing the solvent from the solution to afford amorphous form of Vilazodone hydrochloride.

In another aspect of the present invention, suitable solvent in step (a) is selected from the group of formic acid, acetic acid and propionic acid, more preferably formic acid.

In another aspect present invention provides a process for preparation of a stable and substantially pure amorphous form of Vilazodone hydrochloride, which comprises:
a) Providing a solution of Vilazodone hydrochloride in formic acid;
b) Optionally, filtering the solvent solution to remove any extraneous matter; and
c) Substantially removing the solvent from the solution to afford amorphous form of Vilazodone hydrochloride.

In another aspect present invention provides a process for preparation of a stable and substantially pure amorphous form of Vilazodone hydrochloride, which comprises:
a) Providing a solution of Vilazodone free base in a suitable solvent or a mixture of solvents capable of dissolving Vilazodone;
b) Mixing with the solution of hydrochloric acid dissolved in the suitable solvent;
c) Optionally, filtering the solvent solution to remove any extraneous matter; and
d) Substantially removing the solvent from the solution to afford amorphous form of Vilazodone hydrochloride.

In another aspect of the present invention, suitable solvent in step (a) is selected from the group of formic acid, acetic acid and propionic acid, more preferably formic acid and suitable solvent in step (b) is selected from group comprising water, alcohols, ketones, chlorinated hydrocarbons, hydrocarbons, nitriles, esters, cyclic ethers, aliphatic ethers, polar aprotic solvents, and mixtures thereof. Preferable solvents are chlorinated hydrocarbons, ketones, alcohols and mixtures thereof, more preferably 2-propanol.

In another aspect present invention provides a process for preparation of a stable and substantially pure amorphous form of Vilazodone hydrochloride, which comprises:
a) Providing a solution of Vilazodone free base in formic acid;
b) Mixing with the solution of 2-propanol.HCl;
c) Optionally, filtering the solvent solution to remove any extraneous matter; and
d) Substantially removing the solvent from the solution to afford amorphous form of Vilazodone hydrochloride.

In another aspect, the present invention provides a method of treating a depressive disorder, the method comprising: administering to a patient in need thereof an effective amount of a compound which is a amorphous hydrochloride salt of 1-[4-(5-cyanoindol-3-yl)butyl]-4-(2-carbamoyl-benzofuran-5-yl)-piperazine, wherein a depressive disorder is treated in the patient.

DETAILED DESCRIPTION OF THE INVENTION

Figure 1:
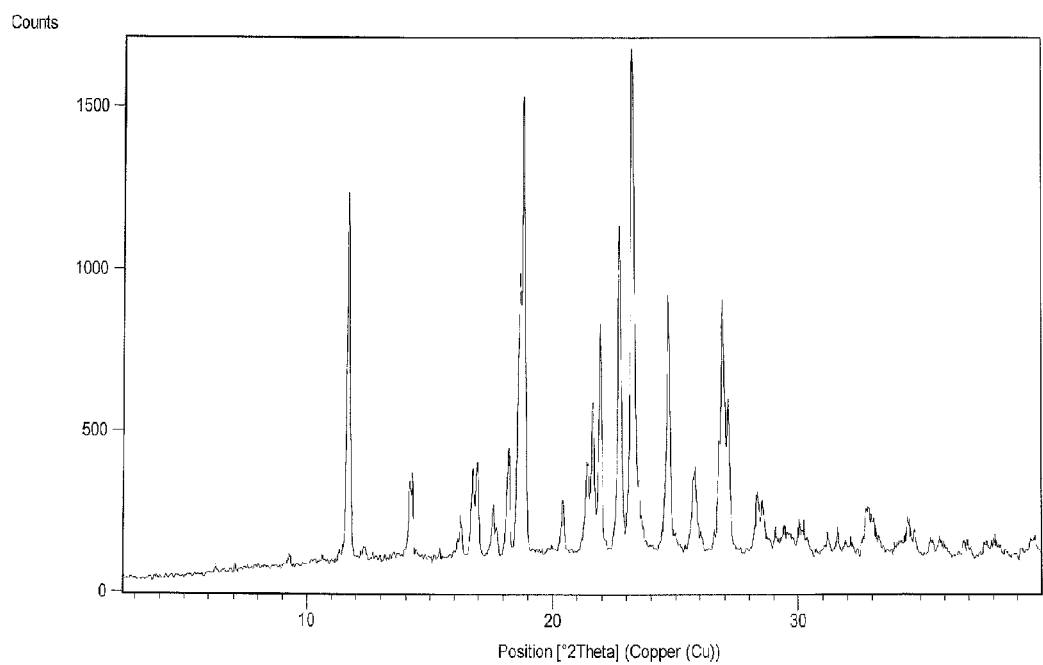
FIG. 1 shows an X-ray diffraction pattern of novel form II of ethyl 5-(4-(4-(5-cyano-1H-indol-3-yl)butyl) piperazin-1-yl)benzofuran-2-carboxylate hydrochloride prepared by inventors.
Figure 2:
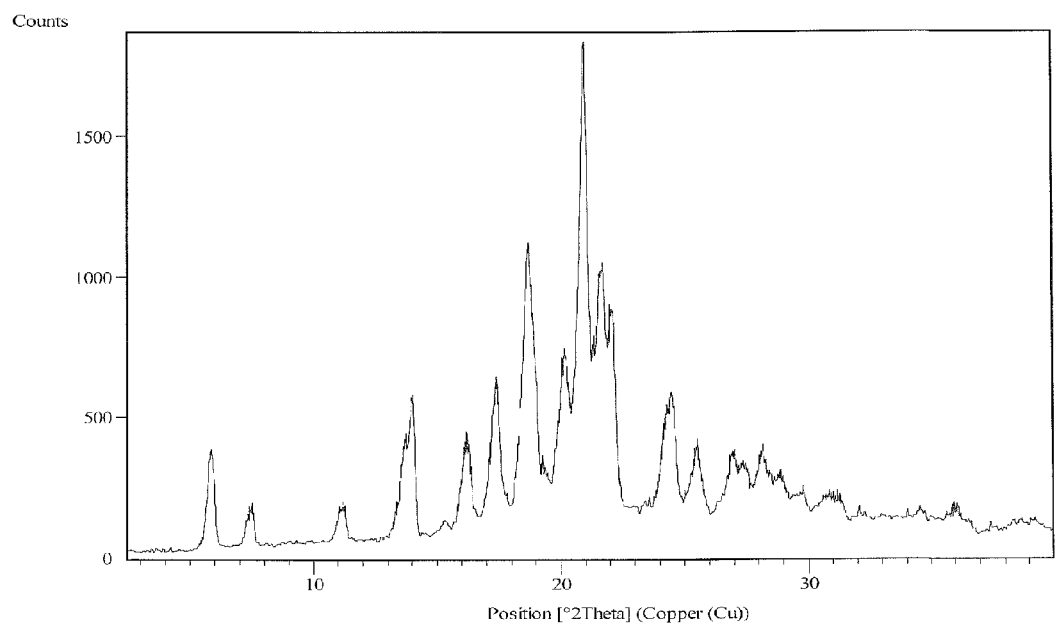
FIG. 2 shows an X-ray diffraction pattern of novel form A of vilazodone prepared by inventors.
Figure 3:
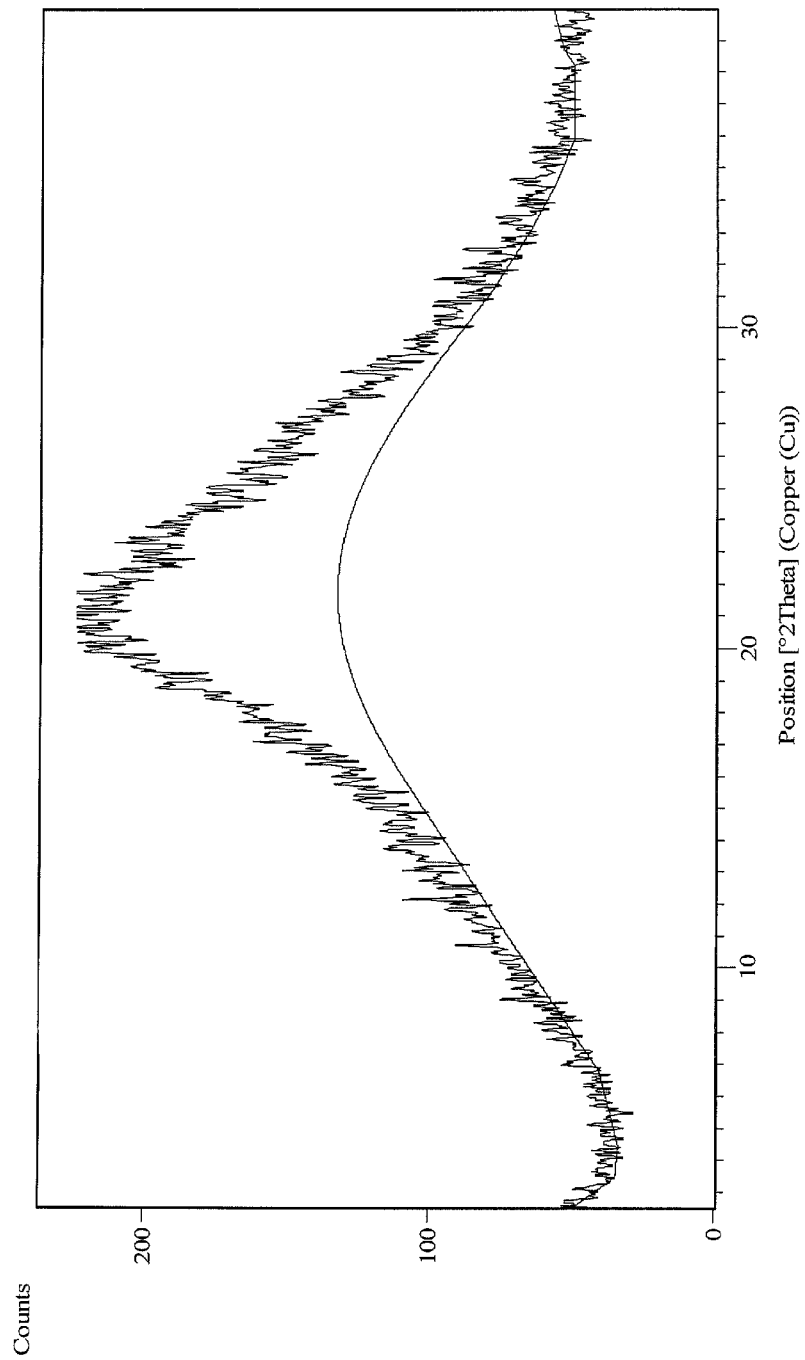
FIG. 3 shows an X-ray diffraction pattern of novel pure amorphous form of vilazodone hydrochloride prepared by inventors.

The present invention provides a process for preparing vilazodone or a salt thereof, comprising a step of obtaining a compound of formula I or a salt there of, from compound of formula II.

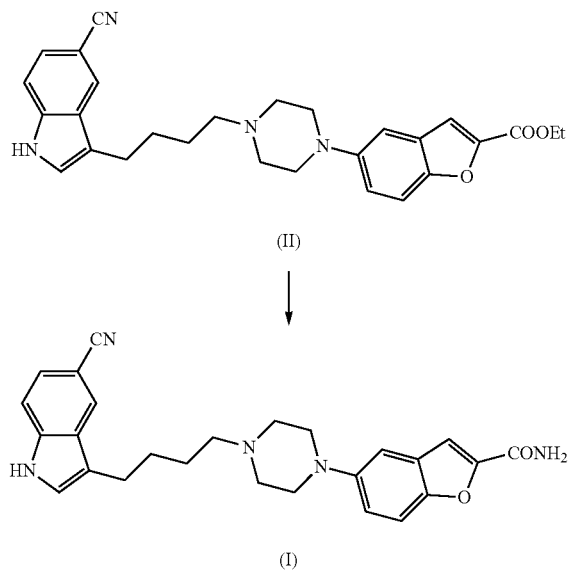

Therefore, in one embodiment the present invention provides a process for preparation of vilazodone a compound of formula (I) or a salt thereof, comprising a step of reacting compound of formula II with source of ammonia to get a compound of formula (I).

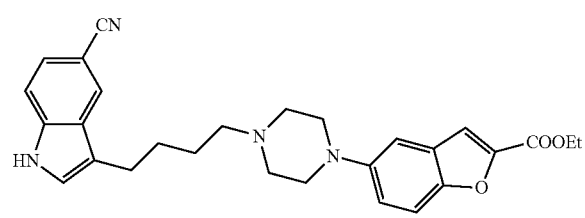

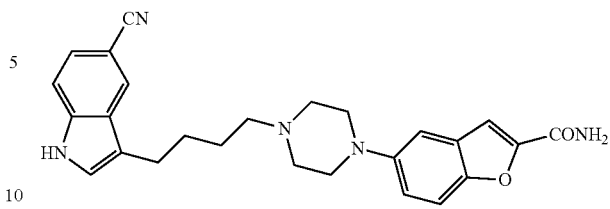

Therefore, in another embodiment the present invention provides a process for preparation of vilazodone or a salt thereof, comprising a step of obtaining a compound of formula I or a salt there of, from compound of formula II in presence of source of ammonia and any suitable solvent.

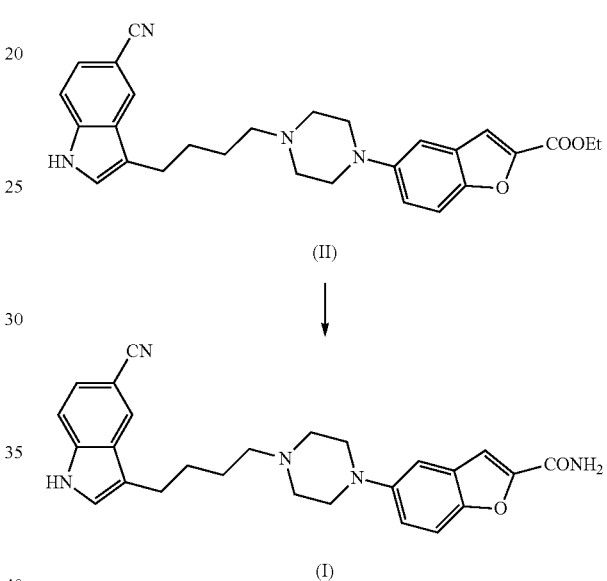

Source of ammonia is selected from ammonia gas, liquid ammonia, aqueous ammonia, ammonium hydroxide, magnesium nitride and formamide with base; more preferably ammonia gas. Suitable solvent is selected from water, alcohols, ketones, diols, triols, esters, amides, ethers, hydrocarbons, polar aprotic solvents, polar solvents, chloro solvents, nitriles or mixtures thereof polar aprotic solvents such as acetone, DMF, acetonitrile, DMSO, sulfolane; alcohols such as methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether, N,N,-dimethyl acetamide, PEG 300, propylene glycol; chloro solvents like methylene chloride, chloroform and ethylene chloride; hydrocarbon solvents like toluene, xylene, heptane, cyclohexane and hexane; more preferably DMSO.

Therefore, in another embodiment the present invention provides a process for preparation of vilazodone or a salt thereof, comprising a step of obtaining a compound of formula I or a salt there of, from compound of formula II in presence suitable solvent under ammonia gas pressure.

Therefore, in another embodiment the present invention provides a novel compound ethyl 5-(1-piperazinyl)-benzofuran-2-carboxylate dihydrochloride.

Therefore, in another embodiment the present invention provides a novel compound ethyl 5-(1-piperazinyl)-benzofuran-2-carboxylate hydrobromide.

Therefore, in another embodiment the present invention provides a process for preparation of ethyl 5-(1-piperazinyl)-benzofuran-2-carboxylate dihydrochloride comprises reaction of compound of formula (VI) with Bis(2-chloroethyl) amine hydrochloride in presence of suitable base, suitable solvent and phase transfer catalyst.

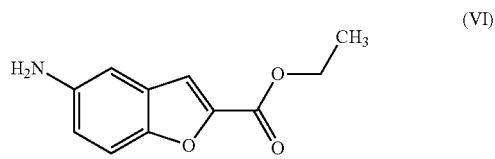

(VI)

Phase transfer catalyst is one selected from the group consisting of quaternary ammonium cations, quaternary phosphonium cations, and cyclic polyethers such as tricaprylylmethylammonium chloride, methyl tributyl ammonium chloride, methyl tributyl ammonium fluoride, tetrabutyl ammonium bromide, tetrabutyl ammonium fluoride, tetrabutyl ammonium hydrogen sulfate, triethyl benzyl ammonium chloride, tetrabutyl phosphonium bromide, tetrabutyl phosphonium chloride, tetraoctylphosphonium bromide, and mixtures thereof. Suitable solvent is selected from water, alcohols, ketones, diols, triols, esters, amides, ethers, hydrocarbons, polar aprotic solvents, polar solvents, chloro solvents, nitriles or mixtures thereof. Polar aprotic solvents such as acetone, DMF, acetonitrile, DMSO, sulfolane; alcohols such as methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether, N,N,-dimethyl acetamide, PEG 300, propylene glycol; chloro solvents like methylene chloride, chloroform and ethylene chloride; hydrocarbon solvents like toluene, xylene, heptane, cyclohexane and hexane, more preferably DMSO. Suitable base is selected from the group of alkali or alkaline earth metal hydroxide, carbonate, bicarbonate.

Therefore, in another embodiment the present invention provides a process for preparation of vilazodone or a salt thereof, comprising purification of vilazodone base with any suitable solvent and suitable base optionally in presence of water, wherein suitable solvent is selected from group of polar aprotic solvents such as acetone, DMF, acetonitrile, DMSO, sulfolane, DMAC, NMP etc. Suitable base is selected from the group of alkali or alkaline earth metal hydroxide, carbonate, bicarbonate. wherein the suitable base is selected from NaOH, KOH, LiOH, NaHCO$_3$, KHCO$_3$, LiHCO$_3$, Na$_2$CO$_3$, K$_2$CO$_3$, Li$_2$CO$_3$, Mg(OH)$_2$, Ca(OH)$_2$, CaCO$_3$, MgCO$_3$, Ba(OH)$_2$, Be(OH)$_2$, BaCO$_3$, SrCO$_3$ and the like or mixtures thereof.

Therefore, in another embodiment the present invention provides a process for preparation of vilazodone or a salt thereof, comprising purification of vilazodone base by treatment of vilazodone base with DMF and aqueous sodium hydroxide solution.

Therefore, in another embodiment the present invention provides a novel compound process for preparation of vilazodone or a salt thereof, comprising crystallizing vilazodone base from DMSO and water.

Therefore, in another embodiment the present invention provides a process having a content of 5-(4-[4-(5-cyano-1H-indol-3-yl)butyl]piperazin-1-yl)benzofuran-2-carboxylic acid is less than 1% by mole; more preferably less than 0.5% by mole; more specifically less than 0.15% by mole.

Therefore, in another embodiment the present invention provides a novel compound novel crystalline form A of Vilazodone.

Therefore, in another embodiment the present invention provides a novel compound Crystalline form A of Vilazodone, having an X-ray diffraction pattern comprising at least five peaks selected from 2theta values 5.8, 13.9, 18.6, 20.9, 21.9±0.3.

Therefore, in another embodiment the present invention provides a process for preparing crystalline form A of vilazodone base, comprising the steps of: (a) dissolving vilazodone base in one or more organic solvent(s), (b) causing crystalline form A to precipitate from the solution obtained in step (a), and (c) isolating the crystalline form A obtained in step (b).

Therefore, in another embodiment the present invention provides a novel compound amorphous vilazodone base.

Therefore, in another embodiment the present invention provides a process for preparing amorphous vilazodone base, comprising the steps of: (a) dissolving vilazodone base in one or more organic solvent(s), (b) causing an amorphous solid to precipitate from the solution obtained in step (a), and (c) isolating the amorphous solid obtained in step (b).

Therefore, in another embodiment the present invention provides a novel crystalline form II of ethyl 5-(4-(4-(5-cyano-1H-indol-3-yl)butyl) piperazin-1-yl)benzofuran-2-carboxylate hydrochloride.

Therefore, in another embodiment the present invention provides a novel compound Crystalline form II of ethyl 5-(4-(4-(5-cyano-1H-indol-3-yl)butyl)piperazin-1-yl)benzofuran-2-carboxylate hydrochloride, having an X-ray diffraction pattern comprising at least five peaks selected from 2theta values 11.7, 18.86, 22.75, 23.3, 24.7±0.3.

Therefore, in another embodiment the present invention provides a process for preparation of vilazodone comprises condensation of compound of formula (VII) or salt thereof with compound of formula (VIII) to get compound of formula (II) or salt thereof in presence of triethyl amine and tetrabutyl ammonium bromide.

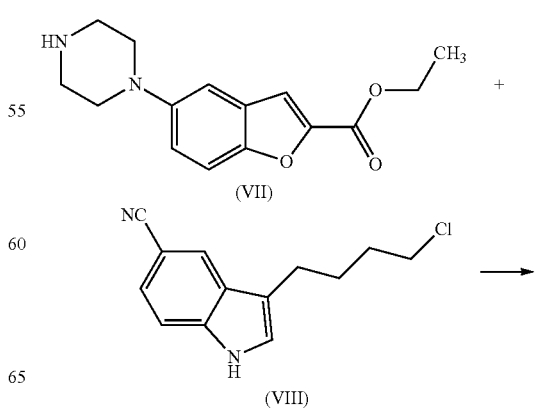

-continued

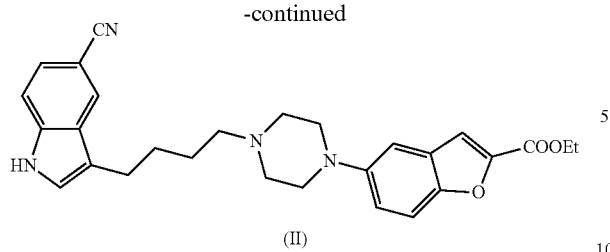

(II)

Therefore, in another embodiment the present invention provides a process for preparation of vilazodone comprises condensation of compound of formula (VII) hydrobromide salt with compound of formula (VIII) to get compound of formula (II).

Therefore, in another embodiment the present invention provides a process for the preparation of vilazodone or a salt thereof which comprises, a. reacting 5-nitro salicaldehyde of formula (III) with 2-bromo diethyl malonate of formula (IV) to get compound of formula (V),

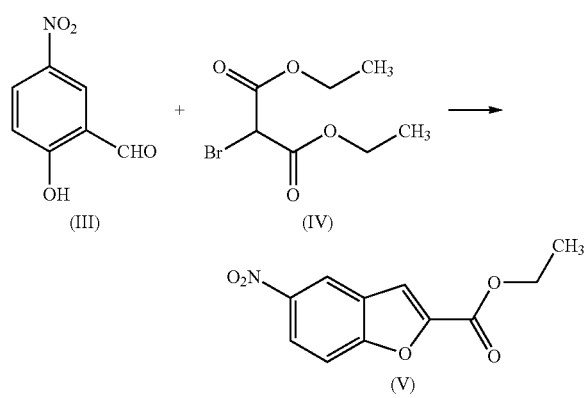

b. reducing compound of formula (V) to get compound of formula (VI)

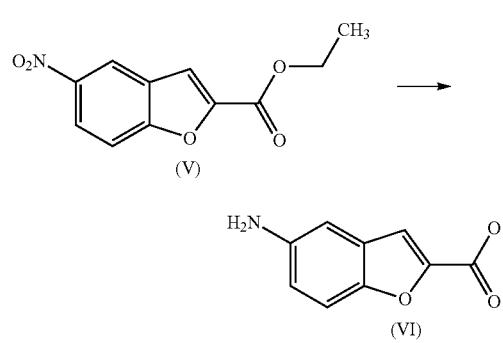

c. converting compound of formula (VI) to compound of formula (VII),

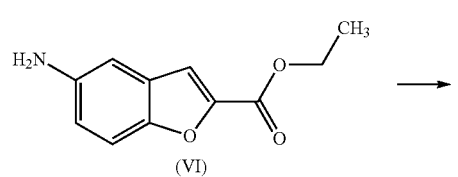

-continued

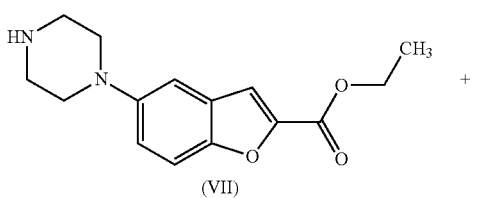

(VII)

d. Condensing compound of formula (VII) or salt thereof with compound of formula (VIII) to get compound of formula (II) or salt thereof,

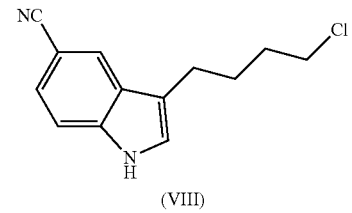

(VII)

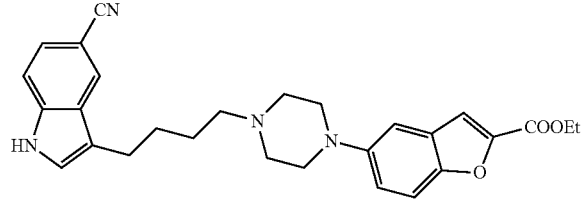

(VIII)

(II)

e. reacting compound of formula (II) with source of ammonia to get compound of formula (I)

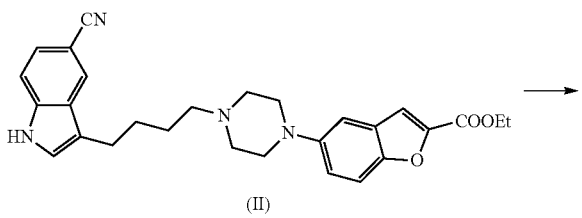

(II)

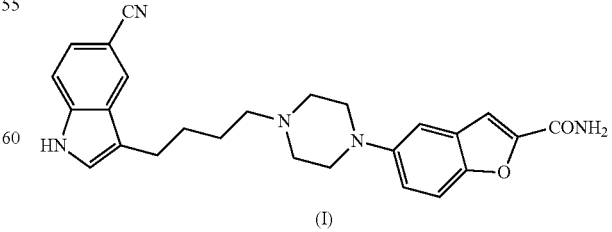

(I)

The embodiments of present invention are shown in below given scheme.

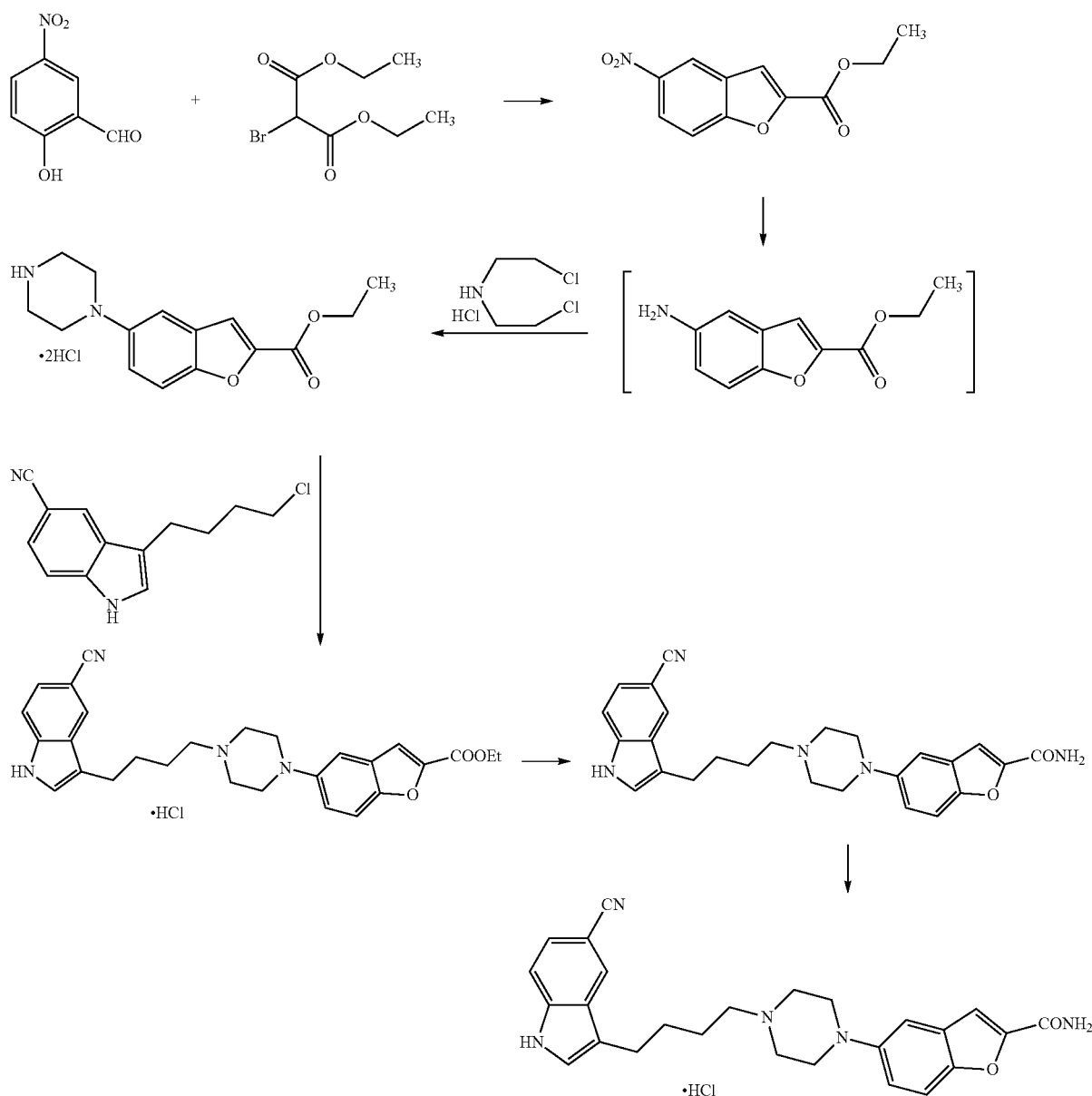
Vilazodone is converted into one of its acid-addition salts by treatment with an acid. In another embodiment present invention provides a process for preparation of 3-(4-chlorobutyl)-1H-indole-5-carbonitrile.
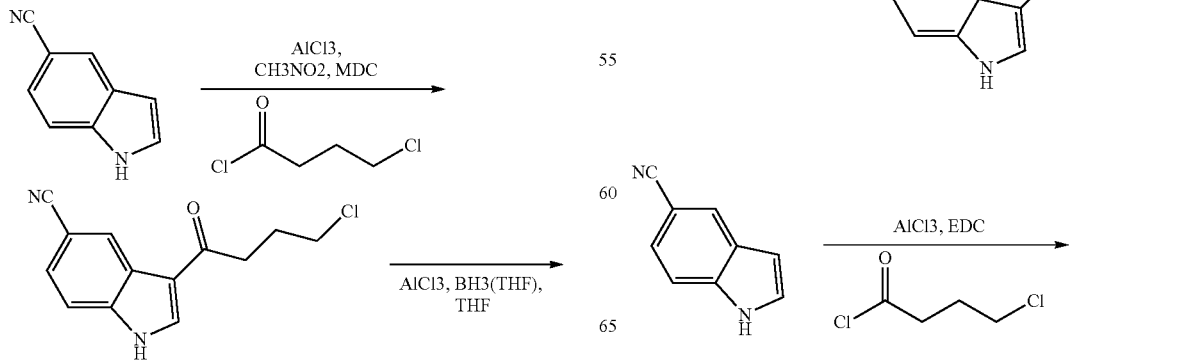

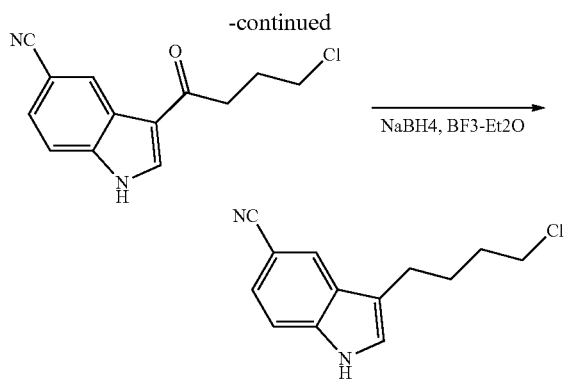

In one embodiment present invention provides novel pure amorphous form of vilazodone hydrochloride.

In another embodiment, the present invention further encompasses a process for preparing the highly pure and stable amorphous form of Vilazodone hydrochloride.

In another embodiment, the present invention provides a pharmaceutical composition comprising amorphous Vilazodone hydrochloride of the present invention and one or more pharmaceutically acceptable excipients.

In another embodiment, the amorphous Vilazodone hydrochloride disclosed herein for use in the pharmaceutical compositions of the present invention, wherein 90 volume-percent of the particles (D90) have a size of less than or equal to about 500 microns, specifically less than or equal to about 300 microns, more specifically less than or equal to about 200 microns, still more specifically less than or equal to about 100 microns, and most specifically less than or equal to about 15 microns.

According to one embodiment of the present invention, there is provided a stable and substantially pure amorphous form of Vilazodone hydrochloride. Amorphous form of Vilazodone hydrochloride is characterized by the following properties: a powder XRD pattern substantially in accordance with FIG. 1. The X-ray powder diffraction pattern shows no peaks, thus demonstrating the amorphous nature of the product.

According to another embodiment of the present invention, a process is provided for preparation of a stable and substantially pure amorphous form of Vilazodone hydrochloride, which comprises:
a) Providing a solution of Vilazodone hydrochloride in a suitable solvent or a mixture of solvents capable of dissolving Vilazodone hydrochloride;
b) Optionally, filtering the solvent solution to remove any extraneous matter; and
c) Substantially removing the solvent from the solution to afford amorphous form of Vilazodone hydrochloride.

The process can produce amorphous Vilazodone hydrochloride in substantially pure form.

The term "substantially pure amorphous form of Vilazodone hydrochloride" refers to the amorphous form of Vilazodone hydrochloride having purity greater than about 98%, specifically greater than about 99%, more specifically greater than about 99.5% and still more specifically greater than about 99.9% (measured by HPLC).

The amorphous Vilazodone hydrochloride obtained by the process disclosed herein is stable, consistently reproducible and has good flow properties, and which is particularly suitable for bulk preparation and handling, and so, the amorphous Vilazodone hydrochloride obtained by the process disclosed herein is suitable for formulating Vilazodone hydrochloride.

The suitable solvent used in step-(a) is selected from the group comprising carboxylic acids, such as formic acid, acetic acid, propionic acid etc.

Step-(a) of providing a solution of Vilazodone hydrochloride includes dissolving Vilazodone hydrochloride in the solvent, or obtaining an existing solution from a previous processing step. Preferably the Vilazodone hydrochloride is dissolved in the solvent at a temperature of below about boiling temperature of the solvent used, more preferably at about 20° C. to about 110° C., and still more preferably at about 25° C. to about 80° C.

The solution in step-(a) may also be prepared by reacting Vilazodone free base with Hydrochloric acid to produce a solution containing Vilazodone hydrochloride, or optionally subjecting the solution to usual work up such as washings, extractions etc., and dissolving the resulting Vilazodone hydrochloride in a suitable solvent at a temperature of below about boiling temperature of the solvent used, more preferably at 20° C. to about 110° C., and still more preferably at about 25° C. to about 80° C.

The solution obtained in step-(a) may optionally be subjected to carbon treatment. The carbon treatment can be carried out by methods known in the art, for example by stirring the solution with finely powdered carbon at a temperature of below about 70° C. for at least 15 minutes, preferably at a temperature of about 25° C. to about 70° C. for at least 30 minutes; and filtering the resulting mixture through hyflo to obtain a filtrate containing Vilazodone hydrochloride by removing charcoal. Preferably, finely powdered carbon is an active carbon.

The solution obtained in step-(a) or step-(b) is optionally stirred at a temperature of about 30° C. to the reflux temperature of the solvent used for at least 20 minutes, and preferably at a temperature of about 40° C. to the reflux temperature of the solvent used from about 30 minutes to about 4 hours.

Removal of solvent in step-(c) is accomplished by, for example, substantially complete evaporation of the solvent, concentrating the solution and filtering the solid under inert atmosphere. Alternatively, the solvent may also be removed by evaporation.

Evaporation can be achieved at sub-zero temperatures by the lyophilisation or freeze-drying technique. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying.

The distillation process can be performed at atmospheric pressure or reduced pressure. Preferably the solvent is removed at a pressure of about 760 mm Hg or less, more preferably at about 400 mm Hg or less, still more preferably at about 80 mm Hg or less, and most preferably from about 30 to about 80 mm Hg.

The substantially pure amorphous Vilazodone hydrochloride obtained by the above process may be further dried in, for example, Vacuum Tray Dryer, Rotocon Vacuum Dryer, Vacuum Paddle Dryer or pilot plant Rota vapor, to further lower residual solvents.

The total purity of the amorphous Vilazodone hydrochloride obtained by the process disclosed herein is of greater than about 99%, specifically greater than about 99.5%, and more specifically greater than about 99.9% as measured by HPLC.

According to another aspect of the present invention, a process is provided for preparation of a stable and substantially pure amorphous form of Vilazodone hydrochloride, which comprises:
a) Providing a solution of Vilazodone free base in a suitable solvent or a mixture of solvents capable of dissolving Vilazodone;
b) Mixing with the solution of hydrochloric acid dissolved in the suitable solvent;
c) Optionally, filtering the solvent solution to remove any extraneous matter; and
d) Substantially removing the solvent from the solution to afford amorphous form of Vilazodone hydrochloride.

The suitable solvent used in step-(b) is selected from the group comprising water, alcohols, ketones, chlorinated hydrocarbons, hydrocarbons, nitriles, esters, cyclic ethers, aliphatic ethers, polar aprotic solvents, and mixtures thereof. Preferable solvents are alcohols and, more preferably isopropyl alcohol.

Exemplary alcohol solvents include, but are not limited to, C1 to C8 straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol.

Exemplary ketone solvents include, but are not limited to, acetone, methyl ethyl ketone, methyl isobutyl ketone, methyl tert-butyl ketone and the like, and mixtures thereof. Exemplary nitrile solvents include, but are not limited to, acetonitrile, propionitrile and the like, and mixtures thereof.

Exemplary ester solvents include, but are not limited to, ethyl acetate, isopropyl acetate, and the like and mixtures thereof.

Exemplary chlorinated hydrocarbon solvents include, but are not limited to, methylene chloride, ethyl dichloride, chloroform, carbon tetrachloride, and mixtures thereof. Specific chlorinated hydrocarbon solvent is methylene chloride.

Exemplary cyclic ether solvents include, but are not limited to, tetrahydrofuran, dioxane, and the like, and mixtures thereof.

Exemplary aliphatic ether solvents include, but are not limited to, diethyl ether, diisopropyl ether, monoglyme, diglyme and the like, and mixtures thereof.

Exemplary hydrocarbon solvents include, but are not limited to, n-pentane, n-hexane, n-heptane and isomers thereof, cyclohexane, toluene and xylene and the like, and mixtures thereof.

Exemplary polar aprotic solvents include, but are not limited to, N, N-dimethylformaniide, N, N-dimethylacetamide, dimethylsulfoxide, and mixtures thereof.

The present invention further illustrated in detail by the below examples which are however not limit to the scope of the invention.

EXAMPLES

Example-1

Preparation of ethyl 5-nitro-1-benzofuran-2-carboxylate

To a solution of DMF (400 ml), $K_2CO_3$ powder (124.1 g) and 5-nitro salicylaldehyde (100 g) was slowly added Diethyl bromomalonate (171.7 g) at 30-40° C. under Nitrogen atmosphere. The reaction mixture was stirred at 85-90° C. under Nitrogen atmosphere for 15 hours. Cool the reaction mix to 80-85° C. Cyclohexane (500 ml) was added to the reaction mix at 70-85° C. within 1 hour and then stirred the reaction mix at 80-85° C. for 15-30 minutes. The reaction mixture was cooled to 15-20° C. and process water (1000 ml) was added to the reaction mixture at 15-20° C. within 1 hour. The reaction mixture was stirred at 20-30° C. for 1-2 hour and then the solid was filtered and washed with process water (100 ml×5). Dried at 55-60° C. for 8-10 hours. Yield: 95.2%

Example-2

Preparation of ethyl-5-amino-1-benzofuran-2-carboxylate

To a solution of ethyl-5-nitro-1-benzofuran-2-carboxylate (100 g) in Ethyl acetate (800 ml) was added 10% palladium on carbon (4.0 g). The reaction mixture was stirred under an atmosphere of hydrogen at 33-38° C. with 4-5 kg/cm² hydrogen pressure for 4-6 hrs. After completion of the reaction, reaction mixture was filtered through hyflo, washed with ethyl acetate. The filtrate was concentrated in vacuo to give ethyl-5-amino-1-benzofuran-2-carboxylate yield: 100%

Example-3

Preparation of ethyl 5-(1-piperazinyl)-benzofuran-2-carboxylate dihydrochloride ethyl-5-amino-1-benzofuran-2-carboxylate obtained in above step was dissolved in o-Xylene (1500 ml) and then Bis(2-chloroethyl) amine hydrochloride (113.8 g), Potassium carbonate powder (108.6 g) and TBAB (5.0 g) at 20-30° C. was added in the reaction mixture. The reaction mixture was maintained for 32 hrs at 135-140° C. After completion of the reaction solid was filtered and washed it with o-Xylene [100 ml×3], suck it dry. The wet cake was charged in the saturated brine solution under stirring and ammonia solution (100 ml) was added in the reaction mixture at 10-15° C. under stirring. The product was extracted in MDC (1000 ml) and washed subsequently with dilute acetic acid and water. Conc. HCl (100.5 g) was charged in MDC layer and then MDC was removed atmospherically up-to 50° C. Ethanol (700 ml) was charged to the residue and raise the temperature of the suspension to 55-60° C. The reaction mass was cooled for 1-2 hours at 20-30° C. and filtered the solid, washed it with Ethanol [100 ml×3]. Dried at 55-60° C. for 12 hours. Yield: 81.3%

Example-4

Preparation of ethyl 5-(1-piperazinyl)-benzofuran-2-carboxylate hydrobromide ethyl-5-amino-1-benzofuran-2-carboxylate obtained in above step was dissolved in o-Xylene (1500 ml) and then Bis(2-chloroethyl) amine hydrochloride (113.8 g), Potassium carbonate powder (108.6 g) and TBAB (5.0 g) at 20-30° C. was added in the reaction mixture. The reaction mixture was maintained for 32 hrs at 135-140° C. After completion of the reaction solid was filtered and washed it with o-Xylene [100 ml×3], suck it dry. The wet cake was charged in the saturated brine solution under stirring and ammonia solution (100 ml) was added in the reaction mixture at 10-15° C. under stirring. The product was extracted in MDC (1000 ml) and washed subsequently with dilute acetic acid and water. Aqueous HBr was charged in MDC layer and then MDC was removed atmospherically up-to 50° C. Ethanol (700 ml) was charged to the residue and raise the temperature of the suspension to 55-60° C. The reaction mass was cooled for 1-2 hours at 20-30° C. and filtered the solid, washed it with Ethanol [100 ml×3]. Dried at 55-60° C. for 12 hours. Yield: 81.3%

Example-5

Preparation of ethyl 5-(4-[4-(5-cyano-1H-indol-3-yl)butyl]piperazin-1-yl)benzofuran-2-carboxylate hydrochloride A mixture of ethyl 5-(1-piperazinyl)-benzofuran-2-carboxylate dihydrochloride (100 g), 3-(4-chlorobutyl)-1H-indole-5-carbonitrile (63.7 g), triethyl amine (400 ml) and TBAB (88.3 g) were heated at 85-90° C. (reflux) under stirring for 10 hrs. After completion of the reaction Acetone (400 ml) was charged to the residue and reflux the reaction mass at 55-60° C. under stirring for 30-45 minutes. The reaction mass was cooled to 45-50° C. and activated carbon (5.0 g) was charged to reaction mass and again refluxed for 15-30 minutes. The reaction mass was cooled to 15-20° C. and filtered through hyflo and washed with acetone. IPA.HCl (~100 ml) was added to the solution at 50-55° C. in more than 30 minutes to adjust the pH 2.0 under stirring and maintained for 45-60 minutes at reflux. The reaction mix was cooled to 20-30° C. under stirring for 2-3 hours and then maintained at 0-5° C. for 45-60 minutes under stirring. The solid was filtered and washed with Acetone. Dried at 55-60° C. for 4-6 hours. Yield: 83%

Example-6

Preparation of ethyl 5-(4-[4-(5-cyano-1H-indol-3-yl)butyl]piperazin-1-yl)benzofuran-2-carboxylate hydrochloride A mixture of ethyl 5-(1-piperazinyl)-benzofuran-2-carboxylate hydrobromide (100 g), 3-(4-chlorobutyl)-1H-indole-5-carbonitrile (63.7 g), triethyl amine (400 ml) and TBAB (88.3 g) were heated at 85-90° C. (reflux) under stirring for 10 hrs. After completion of the reaction Acetone (400 ml) was charged to the residue and reflux the reaction mass at 55-60° C. under stirring for 30-45 minutes. The reaction mass was cooled to 45-50° C. and activated carbon (5.0 g) was charged to reaction mass and again refluxed for 15-30 minutes. The reaction mass was cooled to 15-20° C. and filtered through hyflo and washed with acetone. IPA.HCl (~100 ml) was added to the solution at 50-55° C. in more than 30 minutes to adjust the pH 2.0 under stirring and maintained for 45-60 minutes at reflux. The reaction mix was cooled to 20-30° C. under stirring for 2-3 hours and then maintained at 0-5° C. for 45-60 minutes under stirring. The solid was filtered and washed with Acetone. Dried at 55-60° C. for 4-6 hours. Yield: 83%

Example-7

Preparation of Vilazodone

To a solution of DMSO (400 ml) and Stage-II (100 g) in the Hydrogenator at 20-30° C. Ammonia gas was charged with 5-6 kg pressure. The reaction mix was maintained to 30-35° C. at 5-6 kg Ammonia pressure for 16-18 hours. After completion of the reaction ammonia gas was released the temperature of reaction mass was raised to 50-55° C. Activated carbon (5.0 g) was charged to the reaction mass at 50-55° C. and maintained at 55-60° C. for 15-30 minutes. The reaction mixture was filtered through hyflo and washed with hot (50-55° C.) DMSO (75 ml). Charged the filtrate in hot DM Water (2000 ml) at 80-85° C. within 1 hour. The reaction mix was maintained at 80-85° C. for 30-45 minutes. The solid was filtered and washed with hot water. Suck dried it. The wet cake (75 g) was charged with DMF (450 ml) and the temperature of reaction mix was raised to 50-55° C. Sodium hydroxide solution (dissolve 9.8 g NaOH in 10 ml DM Water) was added to the reaction mass and activated carbon (3.75 g) at 50-55° C. The reaction mix was maintained at 50-55° C. for 30-45 minutes. The reaction mix was filtered through hyflo and washed with hot (50-55° C.) DMF: DM Water mix [(38.5 ml+19.2 ml)×2]. The reaction mixture was cooled for 2-3 hours at 20-30° C. and filtered the solid. Suck dried it completely. Then again wet cake was dissolved in DMSO (350 ml) at 50-55° C. and charged this clear solution in hot water (1500 ml) at 80-85° C. within 1 hour. Maintain the reaction mix was maintained at 80-85° C. for 30-45 minutes and the solid was filtered and washed with DM Water (75 ml×3) at 80-85° C. Suck it dried. Dried it at 55-60° C. Yield: 81.6%

Example-8

Preparation of Amorphous Form of Vilazodone Hydrochloride

Formic acid (500 ml) and vilazodone base (100 g) and 20% w/w hydrochloric acid were mixed at 20-30° C. under stirring. Activated carbon (5.0 g) was added and reaction mass was stirred for 30-45 minutes at 30-35° C. The reaction mass was filtered hot and washed with hot (30-35° C.) Formic acid (100 ml). The spray dryer aspirator was set at 1400 rpm (vacuum at 50-120 mm), inlet temperature 125-130° C., and air pressure at 3-4 Kg/cm2 and feed pump rate of 2-3 rpm. Then filtrate was spray dried. The material was unloaded and dried in VTD at 85-90° C. for 20-24 hours. Yield: 83.3%

Example-9

Preparation of Amorphous Form of Vilazodone Hydrochloride

Vilazodone hydrochloride (2.0 g) was dissolved in formic acid (10 ml) to obtain clear solution. The solvents were removed completely under vacuum at 40° C. and then dried for 12 hours to give 2.0 g of Vilazodone hydrochloride in amorphous form.

Example-10

Preparation of Amorphous Form of Vilazodone Hydrochloride

Formic acid (500 ml) and vilazodone base (100 g) and IPA.HCl were mixed at 20-30° C. under stirring. Activated carbon (5.0 g) was added and reaction mass was stirred for 30-45 minutes at 30-35° C. The reaction mass was filtered hot and washed with hot (30-35° C.) Formic acid (100 ml). The spray dryer aspirator was set at 1400 rpm (vacuum at 50-120 mm), inlet temperature 125-130° C., and air pressure at 3-4 Kg/cm2 and feed pump rate of 2-3 rpm. Then filtrate was spray dried. The material was unloaded and dried in VTD at 85-90° C. for 20-24 hours.

The invention claimed is:

1. A process for preparation of Vilazodone a compound of formula (I) or a salt thereof, comprising a step of directly converting a compound of formula (II) with a source of ammonia to get a compound of formula (I) in the presence of a suitable solvent under ammonia gas pressure,

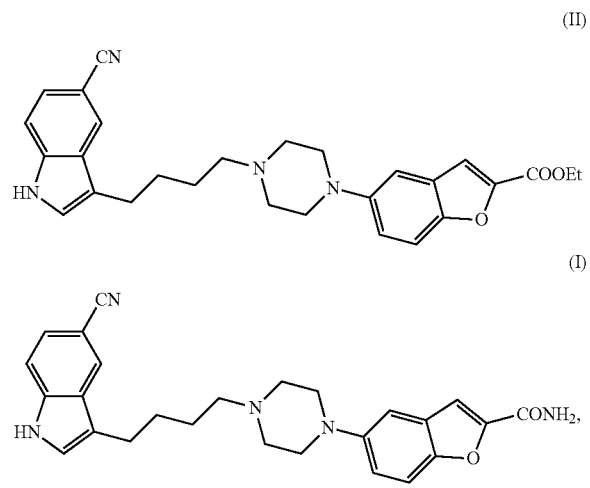

wherein the source of ammonia is ammonia gas.

2. The process as claimed in claim 1, wherein said suitable solvent is selected from water, alcohols, ketones, diols, triols, esters, amides, ethers, hydrocarbons, polar aprotic solvents, polyglycols, pyrrolidones, glycol ethers, polar solvents, chloro solvents, hydrocarbon solvents, nitriles or mixtures thereof; wherein said polar aprotic solvent is selected from the group consisting of acetone, DMF, acetonitrile, DMSO, and sulfolane; wherein said alcohols is selected from the group consisting of methanol, ethanol, propanol, butanol, glycerol, and propylene glycol; wherein said polyglycols is selected from the group consisting of polyethylene glycol 200, polyethylene glycol 300, and polyethylene glycol 400; wherein said pyrrolidones is selected from the group consisting of N-methyl pyrrolidone and 2-pyrrolidone; wherein said glycol ethers is selected from the group consisting of propylene glycol monomethyl ether, dipropylene glycol monomethyl ether, diethylene glycol ethyl ether, N,N,-dimethy acetamide, PEG 300, and propylene glycol; wherein said chloro solvents is selected from the group consisting of methylene chloride, chloroform, and ethylene chloride; wherein said hydrocarbon solvents is selected from the group consisting of toluene, xylene, heptane, cyclohexane, and hexane.

3. The process according to claim 1, further comprising a purification step of Vilazodone base with a suitable solvent and a suitable base optionally in presence of water.

4. The process claimed in claim 3, wherein said suitable solvent is an aprotic solvent selected from group consisting of acetone, DMF, acetonitrile, DMSO, sulfolane, DMAC, and NMP.

5. The process claimed in claim 3, wherein said suitable base is selected from the group consisting of alkali or alkaline earth metal hydroxide, carbonate or bicarbonate.

6. The process claimed in claim 5, wherein the suitable base is selected from the group consisting of NaOH, aqueous sodium hydroxide, KOH, LiOH, NaHCO$_3$, KHCO$_3$, LiHCO$_3$, Na$_2$CO$_3$, K$_2$CO$_3$, Li$_2$CO$_3$, Mg(OH)$_2$, Ca(OH)$_2$, CaCO$_3$, MgCO$_3$, Ba(OH)$_2$, Be(OH)$_2$, BaCO$_3$, SrCO$_3$ and mixtures thereof.

7. The process according to claim 1, further comprising crystallizing Vilazodone base from DMSO and water.

8. The process as claimed in claim 1, wherein the ammonia gas pressure is 5 kg/cm$^2$ to 6 kg/cm$^2$.

* * * * *